United States Patent [19]

Bright

[11] Patent Number: 4,544,779

[45] Date of Patent: Oct. 1, 1985

[54] EXTRACTION OF ALCOHOLS WITH PHOSPHINE OXIDES

[75] Inventor: John H. Bright, Norwalk, Conn.

[73] Assignee: American Cyanamid Company, Stamford, Conn.

[21] Appl. No.: 595,843

[22] Filed: Apr. 2, 1984

[51] Int. Cl.[4] .................... C07C 29/86; C07C 31/08; C07C 31/12

[52] U.S. Cl. .................. 568/918; 568/919; 568/920

[58] Field of Search ................ 568/918, 919, 920

[56] References Cited

U.S. PATENT DOCUMENTS 4,399,000 8/1983 Tedder ........................... 568/918
4,454,359 6/1984 Colgrove et al. ................ 568/918

FOREIGN PATENT DOCUMENTS 310623 5/1929 United Kingdom ............... 568/918

OTHER PUBLICATIONS

Bell, report prepared for the U.S. Dept. of Energy under Contract DE-AC06-76LO 1830, Sep. 1981.

Primary Examiner—J. E. Evans
Attorney, Agent, or Firm—Frank M. Van Riet

[57] ABSTRACT

A method for the extraction of lower alcohols from aqueous solutions by contacting said solutions with various phosphine oxides, in the presence or absence of alkali or alkaline earth metal salts, is disclosed.

11 Claims, No Drawings

EXTRACTION OF ALCOHOLS WITH PHOSPHINE OXIDES

BACKGROUND OF THE INVENTION

The extraction of lower alcohols, especially ethanol, from aqueous solutions thereof, especially very dilute solutions, in order to recover the alcohol has become increasingly important in recent years.

J. W. Roddy, Ind. Eng. Chem. Process Des. Dev., 1981, 20, 104–108 discloses the increased interest in the use of alcohol as an additive to gasoline to improve the octane rating and extend its supply. The use of ethanol, in particular, for this purpose has become increasingly important. Present methods for recovering ethanol, however, have proven expensive in connection with cost and energy consumed because of the need to recover ethanol from water by distillation. Since most ethanol containing waste streams are very dilute in ethanol concentration, distillation has proven to be too costly. It has been determined that a balance between distillation cost and the amount of ethanol recovered centers at aqueous concentrations of ethanol of about 15–25%. Roddy discusses the use of various phosphorus solvents such as triisobutyl phosphate, tris(2-methylbutyl)phosphate, tri-n-butyl phosphate, tris-2-ethylhexyl phosphate and diamyl amyl phosphonate for the extraction of ethanol from aqueous solutions thereof and, although functional, these solvents and the others related therein have not proven to be as effective as at first believed because of their undesirable water-solubility and hydrolytic instability.

U.S. Pat. No. 4,346,241 is directed to the extraction of alcohols from aqueous solutions utilizing liquid secondary amines and aromatic cyclic amines such as quinoline, 4-n-propylpyridine. These extractants, although relatively insoluble in water are not as effective extractants for ethanol as is required because of their instability at temperatures of distillation. The amines decompose into colored species during distillation and are therefore unacceptable as well as being non-recoverable under these conditions.

C. L. Munson et al, Ind. Eng. Chem. Process Des. Dev. 1984, 23, 109–115, have further investigated the factors influencing extraction of ethanol from aqueous solution however, only the extractants disclosed by prior investigation are set forth therein.

Other extractants for ethanol have also been investigated e.g. fluorocarbons (U.S. Pat. No. 4,260,826) and dibutyl phthalate, Science, Oct. 5, 1979. Halogenated hydrocarbons e.g. Freon 11 are impractical because they must be boiled off and recondensed thereby proving costly while dibutyl pthalate hydrolyzes at the distillation temperature of ethanol.

N. E. Bell of Battelle Memorial Institute, Sept. 1981, Pacific Northwest Laboratory, in a report prepared for the U.S. Dept. of Energy under Contract DE-A CO6-76 RLO 1830, available from National Technical Information Service, U.S. Department of Commerce, 5285 Port Royal Road, Springfield, Va. 22151, disclosed that tri-n-octyl phosphine oxide (TOPO) in methyl isobutylketone or kerosene at ratios of 10:90, respectively, and other solvents were used to extract biomass gasification wastewaters which were rich in acetic and propionic acids. The wastewaters also contained ethanol. Two of the solvents investigated were shown to extract ethanol, i.e. n-butanol and methylisobutyl ketone. The report is silent, however, with regard to the extraction of ethanol or any other alcohol by the TOPO based materials investigated.

It can therefore be seen that extensive experimental work is ongoing in connection with the extractors of alcohols from aqueous solution and that if most of the disadvantages of those systems presently uncovered could be overcome, a long-felt need would be satisfied.

SUMMARY OF THE INVENTION

It has now been found that lower alcohols can be extracted from aqueous solutions utilizing extractants comprising various phosphine oxides whereby the difficulties attendant other previously known extractants are avoided. The phosphine oxides of the present invention are water-insoluble and are therefore easily separated from the extraction extract. They are highly efficient alone, in admixture with one another, in conjunction with diluents or on solid supports. The efficiency is enhanced further by the addition of various salts to the solution being extracted.

DESCRIPTION OF THE INVENTION INCLUDING PREFERRED EMBODIMENTS

In accordance with the invention described herein, lower alcohols which are present in aqueous solutions are recovered therefrom in more concentrated form. The process comprises contacting an aqueous solution containing an alcohol having from 2–4 carbons, inclusive, and substantially free of organic acids with a sufficient amount of a phosphine oxide having the formula $$R_3P=O$$

wherein each R, individually, is an alkyl radical of 4–18 carbon atoms, inclusive, a cycloalkyl radical of 6–8 carbon atoms, inclusive, an aralkyl radical of 7–12 carbon atoms, inclusive, or an alkyl substituted aralkyl radical of 8–15 carbon atoms, inclusive, said alkyl substituent having from 1–8 carbon atoms, inclusive, the total number of carbon atoms in said phosphine oxide being at least 16. The extracted solution is then separated from the phosphine oxide compound.

The process of this invention is especially advantageous when applied to the recovery of alcohols e.g. ethanol, propanol, isopropanol, n-, t- or isobutanol, ethyleneglycol, propyleneglycol, butylene glycol and the like, from solutions produced by fermentation, i.e. fermentation liquors; however, any alcohol stream obtained from any other process may also be so treated e.g. water per se, solvent streams and alcoholic beverages such as beer, wines, etc. Most preferred are alcohol streams wherein the alcohol content comprises no more than about 15%, by weight, based on the total weight of the aqueous solution. Because the phosphine oxides used herein are also known extractants for organic acids such as acetic acid etc., the aqueous alcoholic solutions treated herein must be substantially free of such acids. By the term "substantially free", as used herein, is meant that the weight ratio of acid to alcohol is less than 0.1.

Examples of phosphine oxides used herein and falling within the scope of the structural formula set forth above include tri-n-hexylphosphine oxide, tri-n-octylphosphine oxide, tris(2,4,4-trimethylpentyl) phosphine oxide, tricyclohexylphosphine oxide, tri-n-dodecylphosphine oxide, tri-n-octadecyl phosphine oxide, tris(2-ethylhexyl)phosphine oxide, di-n-hexyl-2,4,4-trimethylpentylphosphine oxide, octyldiisobutylphosphine oxide, bis(2-phenethyl)-n-octylphosphine oxide, di-n-hexylisobutylphosphine oxide, octyldiisobutylphosphine oxide, tribenzylphosphine oxide, tris(p-ethylbenzyl)phosphine oxide, di-n-hexylbenzylphosphine oxide and the like. The preferred oxides are tri-n-octylphosphine oxide (TOPO) and tri-n-hexylphosphine oxide (THPO). Even more preferred are mixtures of TOPO and THPO at ratios ranging from 75:25 to 25:75, respectively.

The above-described oxides may be used alone, i.e. neat, or as solutions in a diluent. The diluent may comprise any organic material having a boiling point over about 100° C., preferably over about 110° C. A preferred group of diluents are the aromatic diluents, examples of which include Exxon 100, a 98 vol. % cq compounds, Exxon 150, a 97 vol. % aromatic hydrocarbon containing about 70 vol. % $C_{10}$ and $C_{11}$ compounds (both sold by Exxon Corp.), Kermac 470B (Triangle Industries), a hydrocarbon mixture containing 17 vol. % aromatics, 34 vol. % paraffins and 49 vol. % naphthenes and Nalkylene 550 (Conoco) an alkyl benzene containing $C_{10}$–$C_{14}$ side chains.

The aqueous alcohol solution is contacted in a liquid-liquid extraction, either batch, or continuously countercurrent, with the phosphine oxide solution when a diluent is employed. The ratio of aqueous (A) phase to organic (O) phase is chosen to most efficiently remove the alcohol from the solution.

The phosphine oxide may be used neat as such or supported on a solid carrier or support. Usually the support is inert, however, it is also permissible to use chemically active supports without falling outside the scope of the present invention.

The solid materials or supports for the phosphine oxide extractants of the present invention are preferably water-insoluble adsorbents and include, but are not limited to, such materials as diatomaceous earth, silica, wide-pore carbon, and the like, or crosslinked polymeric materials in the form of porous beads. Synthetic macroporous, crosslinked copolymers of styrene and divinyl benzene are commonly used support materials. Other commonly used supports are, for example, divinylbenzene crosslinked polyacrylates and polymethacrylates. These supports themselves are generally not critical and a convenient support amenable to a particular application may easily be determined by one skilled in the art with simple experimentation.

Liquid membrane extraction as described by Bock, Valint and Hayworth of Exxon Research and Engineering Company and selective supported membrane extraction as described by Obermayer, Nichols, Allen and Caron of the Moleculon Research Corporation may also be used.

Many monovinyl compounds (monomers) can be used alone or combined in the preparation of the polymeric supports useful in the present invention. They include, but are not limited to, styrene, methylstyrene, acrylic acid, methacrylic acid, acrylonitrile, vinyl anisole, vinyl naphthalene; acrylic and methacrylic acid esters, such as methyl-, ethyl-, propyl-, isopropyl-, butyl-, isobutyl-, tert.butyl-, ethyl-, hexyl-, cyclohexyl-, benzyl-, phenyl-, ethoxymethyl-, propoxymethyl-, propoxypropyl-, ethoxyphenyl-, ethoxybenzyl-, ethoxycyclohexyl-, methoxycyclohexyl acrylates and methacrylates; alkylphenyl acrylates and methacrylates; ethylene, propylene, isobutylene, diisobutylene; vinyl chloride; vinyl acetate, vinylidene chloride, and the like. Polyethylenically unsaturated monomers, such as butadiene, isoprene, chloroprene, which behave as if they had only a simple double bond, are also suitable.

Suitable polyvinyl compounds which function as crosslinking agents include, but are not limited to, divinylbenzene, divinylpyridine, divinyltoluene, divinylnaphthalene, diallyl phthalate, divinylxylene, divinylethylbenzene, divinylsulfone, polyvinyl or polyallyl ethers of glycols, glycerine and pentaerythritol, divinylketone, divinyl sulfide, allylacrylate, diallylmaleate, diallylfumarate, diallyl succinate, diallyl carbonate, diallyl malonate, diallyl oxalate, diallyl adipate, diallyl sebacate, divinyl sebacate, diallyl silicate, triallyl phosphate, N,N'-methylenediacrylamide, N,N'-methylenedimethacrylamide, N,N'-methylenediacrylamide, trivinylbenzene, trivinylnaphthalene, and the like. The amount of polyvinyl compound used may vary over wide limits. In general, however, the polyvinyl compound is used in an amount ranging from about 5 to 70% by weight, based on the total weight of monomers, and preferably between about 8 and 60% by weight.

The phosphine oxide extractant compound may be incorporated in or on the support material by any convenient technique. Conventional and applicable techniques include, but are not limited to, impregnation, with the aid of a solvent, or by encapsulation, through the addition of the extractant to the monomer mixture, adding a polymerization catalyst, and then polymerizing the resulting mixture or solution of monomers in the presence of the extractant by conventional techniques. A procedure for the encapsulation of extractants via this technique is described by Krobel et al, U.S. Pat. No. 3,960,762.

In addition to the polymeric cross-linked macroporous polymers described above, the present invention may utilize as the polymeric support material crosslinked macroporous copolymers containing phosphine oxide functions directly bonded to the polymer backbone. An example of such a polymer is a copolymer of styrene, chloromethyl styrene and divinylbenzene or a copolymer of p-chloromethyl styrene and divinylbenzene wherein the chloromethyl group is reacted with a secondary phosphine oxide, e.g., dioctylphosphine oxide; see, for example, European Patent Application 0031761 to Bolleau et al. Similar polymers are described by McKinley et al, U.S. Pat. No. 3,708,462.

Alternatively, certain crystalline phosphine oxides, such as tribenzylphosphine oxide, may be used alone, or mixed with an inert solid material, as a support for extraction of alcohols. Thus, a solution containing alcohols to be extracted may be slurried with the solid phosphine oxide or passed through a column packed with the solid phosphine oxide or a mixture thereof with an inert solid material.

The amount of phosphine oxide incorporated in or on the support material by impregnation or encapsulation, or by the use of polymers containing phosphine oxide groups, or by the use of crystalline phosphine oxides alone, may vary over wide limits, provided sufficient phosphine oxide is available to extract the alcohols from solutions containing them. Ordinarily, the need for efficiency of extraction will determine the amount of phosphine oxide extractant used and these levels can be easily determined by the skilled artisan by sample experimentation.

The extraction may be conducted at about the temperature of the aqueous alcohol feed or at temperatures approaching the boiling point of the alcohol-extractant mixture. Elevated temperatures may be used but require energy input and therefore room temperature is preferred.

A further feature of the instant process is the addition of an alkali or alkaline earth metal salt to the aqueous alcohol solution or in conjunction with the phosphine oxide extractant in amounts ranging from about 2% to about 45%, preferably from about 5% to about 25%, by weight, based on the total weight of the aqueous alcohol solution. The presence of such a salt increases the amount of alcohol extracted and results in an increased alcohol concentration in the alcohol-water extracted. Suitable salts include the halides, carbonates, phosphates, sulfates, etc. of sodium, potassium, lithium, magnesium, calcium, barium and the like. The preferred salts are those of sodium, potassium, and magnesium. The most preferred salt is sodium chloride.

The following examples are set forth for purposes of illustration only and are not to be construed as limitations on the present invention except as set forth in the appended claims. All parts and percentages are by weight unless otherwise specified.

EXAMPLE 1

To a suitable reaction vessel is charged a 10 wt. % aqueous solution of ethanol and a diluent solution of a phosphine oxide. The vessel is sealed and the contents stirred for 15 minutes at 25° C. The results are set forth in Table I, below.

TABLE I

| Run | Phosphine Oxide | wt. % | Diluent | A/O | wt. % Ethanol Extracted |
|---|---|---|---|---|---|
| a | TOPO | 39 | Heptane | .23 | 59 |
| b | THPO/TOPO 50/50 | 80 | Heptane | .43 | 70 |
| c | TOPO | 39 | Exxon 100 | .19 | 65 |
| d | NONE | 0 | Heptane | .23 | 4 |

TOPO = tri-n-octylphosphine oxide
THPO = tri-n-hexylphosphine oxide

EXAMPLE 2

Following the procedure of Example 1 except that the extractant is a 65/35 mixture of THPO and TOPO, the A/O is 0.2 and 250 parts/L of the extractant are used, a series of diluents is compared. The aqueous ethanol solution is at 8 wt. percent. The results are set forth in Table II, below.

TABLE II

| Run | Diluent | wt % Ethanol Extracted | wt. % Ethanol in Extracted Ethanol/Water |
|---|---|---|---|
| a | Decane | 60 | 42 |
| b | Exxon/150 | 62 | 44 |
| c | Nalkylene 550 | 59 | 42 |
| d | Kermac 470B | 59 | 43 |

EXAMPLE 3

The procedure of Example 1 is again followed except that the aqueous ethanol solution concentration is 3.1 wt. %, the extractant is a 70/30 mixture of THPO and TOPO, the diluent is Exxon 150 and the A/O is 0.8. The results are disclosed in Table III, below.

TABLE III

| Run | Extractant Conc. parts/L | Wt. % Ethanol Extracted | Wt. % Ethanol in Extracted Ethanol-Water |
|---|---|---|---|
| a | 870 (neat) | 52 | 14 |
| b | 700 | 53 | 16 |
| c | 500 | 40 | 22 |
| d | 300 | 34 | 31 |
| e | 170 | 27 | 45 |
| f | Exxon 150 only | 6 | — |

EXAMPLE 4

The procedure of Example 3 is again followed except that the concentration of ethanol in the charge in Runs a-f is 8 wt. % and in Runs g-i is 9 wt. %, a salt (NaCl) is added in some runs. Table IV reports the results.

TABLE IV

| Run | Salt wt % | Extractant Conc. pts/l | Wt. % Ethanol Extracted | Wt. % Ethanol in Extracted Ethanol/Water |
|---|---|---|---|---|
| a | 0 | 250 | 35 | 70 |
| b | 0 | 500 | 47 | 24 |
| c | 0 | 870 (neat) | 49 | 40 |
| d | 10 | 250 | 39 | 76 |
| e | 10 | 500 | 60 | 57 |
| f | 10 | 870 (neat) | 61 | 42 |
| g | 20 | 250 | 52 | 85 |
| h | 20 | 500 | 70 | 72 |
| i | 20 | 870 (neat) | 71 | 61 |

EXAMPLE 5

Again following the procedure of Example 1 a liquid phosphine oxide mixture comprising 26 wt. % of THPO; 42 wt. % of di-n-hexyl-n-octyl phosphine oxide; 24 wt. % of n-hexyl-di-n-octylphosphine oxide and 8 wt. % TOPO, and Exxon 150 is used to extract a commercially available beer containing 2.95 wt. % ethanol. TOPO is also used alone. The results are set forth in Table V, below.

TABLE V

| Run | A/O | Wt. % Ethanol Extracted | Wt. % Ethanol in Extracted Ethanol-water | Moles P.O./ Moles Ethanol |
|---|---|---|---|---|
| a* | 1 | 45 | not tested | 3.9 |
| b[1] | 0.5 | 54 | 24 | 4.5 |
| c[2] | 1 | 17 | — | 0.6 |

* = no diluent present
1 = 500 parts/L extractant used in Exxon 150
2 = 150 parts/L TOPO in heptane The separation rate for Run a is very slow, for Run b is slow and for Run c is fast. Runs a and b exhibited a definite third phase while Run c shows only a slight third phase. Run a is colorless, Run b is light amber, and Run c is hazy amber.

EXAMPLE 6

Following the procedure of Example 1, a 2.8 wt. % aqueous ethanol solution is extracted with various concentrations of extractant of Example 5 in Exxon 150. Results are seen in Table VI, below.

TABLE VI

| Run | A/O | Extractant Concentration | Wt. % Ethanol Extracted | Wt. % Ethanol in Extracted Ethanol-water |
|---|---|---|---|---|
| a | 1.4 | 870 (neat) | 29 | 16 |
| b | 1.3 | 800 | 32 | 16 |
| c | 1.0 | 642 | 39 | 25 |
| d | 0.8 | 500 | 36 | 22 |
| e | 0.6 | 400 | 39 | 29 |
| f | 0.4 | 250 | 43 | 32 |
| g | 0.2 | 125 | 46 | 65 |
| h | 0.2 | diluent only | 7 | — |

EXAMPLE 7

A 1.4 wt. % aqueous butanol solution is extracted, in accordance with the procedure of Example 1, with a mixture of 8.5 wt. % of THPO; 33 wt. % of di-n-hexyl-n-octylphosphine oxide; 41 wt. % of n-hexyl-di-n-octyl-phosphine oxide; 18 wt. % of TOPO. The results are set forth in Table VII, below.

TABLE VII

| Run | A/O | Wt. % Butanol Extracted | Wt. % Butanol in Extracted Butanol-Water |
|---|---|---|---|
| a | 0.2 | 99 | 3.8 |
| b | 0.5 | 97 | 8.3 |
| c | 1.0 | 93 | 19 |
| d | 2.0 | 88 | 29 |
| e | 5.0 | 69 | 49 |
| f | 10.0 | 68 | 63 |
| g | 20.0 | 39 | 72 |
| h | 50.0 | 21 | 77 |

EXAMPLE 8

Diatomaceous earth (D.E.) or polystyrene (P.S.) is added to a hexane solution of extractant to form a slurry which is then stirred and heated to evaporate the hexane. The resultant supported extractant is packed in 14.5 × 100–300 mm. columns and used to aqueous ethanol solutions. Results are set forth below in Table VIII.

TABLE VIII

| Run | Support | Extractant wt % | Ethanol wt % Feed/Effluent | | % Ethanol Extracted |
|---|---|---|---|---|---|
| a | D.E. | — | 2.50 | 2.48 | 1 |
| b | D.E. | TOPO-50 | 2.48 | 2.16 | 19 |
| c | D.E. | THPO/TOPO[1]-50 | 2.34 | 0.49 | 79 |
| d | D.E. | THPO/TOPO[1]-20 | 9.7 | 5.99 | 38 |
| e | P.S. | THPO/TOPO[1]-20 | 9.7 | 7.64 | 21 |

[1] = 27–25 wt. % TOPO + 73–72 wt. % THPO

EXAMPLE 9

A 3 wt. % aqueous ethanol solution is extracted at 21°–23° C. and an A/O of 1.0 utilizing two quinoline compounds of U.S. Pat. No. 4,346,241 and the extractant of Example 5. The results are set forth in Table IX below.

TABLE IX

| Run | Extractant-wt. % | % Ethanol Extracted | wt. % Ethanol in Extracted Ethanol-Water |
|---|---|---|---|
| a | Ex. 5 - | 42 | 16 |
| b | Quinoline | 40 | 7 |
| c | 5,6,7,8-Tetra-hydroquinoline | 46 | 7 |

EXAMPLES 10–16

Following the procedure of Example 5, the following various extractants are used to treat the aqueous ethanol solution thereof. In each instance, excellent extraction of ethanol is achieved.

| Example 10 | tris(2,4,4-trimethylpentyl) phosphine oxide |
|---|---|
| Example 11 | tricyclohexyl phosphine oxide |
| Example 12 | tri-n-dodecyl phosphine oxide |
| Example 13 | tris(2-ethylhexyl) phosphine oxide |
| Example 14 | n-hexyl-bis(2,4,4-trimethylpentyl) phosphine oxide |
| Example 15 | tribenzyl phosphine oxide |
| Example 16 | bis(2-phenethyl)n-octyl phosphine oxide |

EXAMPLES 17–19

The use of (17) sodium sulfate, (18) calcium chloride, and (19) potassium carbonate, in lieu of the sodium chloride of Example 4 results in extractions similar in effectiveness to those shown therein.

What is claimed:

1. A method for recovering lower alcohols from aqueous solutions thereof in some concentrated form which comprises contacting an aqueous solution containing an alcohol having from 2–4 carbon atoms, inclusive, and a weight ratio of acid to alcohol of less than 0.1 with a sufficient amount of a phosphine oxide having the formula $$R_3P=O$$

wherein each R, individually, is an alkyl radical of 4–18 carbon atoms, inclusive, or a cycloalkyl radical of 6–8 carbon atoms, inclusive, the total number of carbon atoms in said phosphine oxide being at least 16, to extract said alcohol and separating the extracted solution from said phosphine oxide compound.

2. A method according to claim 1 wherein said phosphine oxide is tri-n-octylphosphine oxide.

3. A method according to claim 1 wherein said phosphine oxide is tri-n-hexylphosphine oxide.

4. A method according to claim 1 wherein said phosphine oxide is a mixture of tri-n-octylphosphine oxide and tri-n-hexylphosphine oxide.

5. A method according to claim 1 which comprises adding an alkali or alkaline earth metal salt to said aqueous solution before or during contact thereof with said phosphine oxide.

6. A method according to claim 1 wherein said aqueous alcohol solution is a product of fermentation.

7. A method according to claim 1 wherein said aqueous alcohol solution is a beer.

8. A method according to claim 1 wherein said phosphine oxide is used in conjunction with a diluent therefor.

9. A method according to claim 1 wherein said phosphine oxide is employed on a solid support therefor.

10. A method according to claim 1 wherein said phosphine oxide is a mixture of tri-n-octylphosphine oxide, tri-n-hexylphosphine oxide, di-n-octylhexylphosphine oxide and di-n-hexyloctylphosphine oxide.

11. A method according to claim 1 wherein said phosphine oxide is a neat liquid.

* * * * *